(12) United States Patent
Williams et al.

(10) Patent No.: US 10,775,363 B2
(45) Date of Patent: Sep. 15, 2020

(54) NON-CONTACT SOILAGE DETECTOR AND FLASHLIGHT

(71) Applicants: Richard E. Williams, Knoxville, TN (US); Owen Keith Neely, Powell, TN (US)

(72) Inventors: Richard E. Williams, Knoxville, TN (US); Owen Keith Neely, Powell, TN (US)

(*) Notice: Subject to any disclaimer, the term of this patent is extended or adjusted under 35 U.S.C. 154(b) by 306 days.

(21) Appl. No.: 16/015,594

(22) Filed: Jun. 22, 2018

(65) Prior Publication Data

US 2018/0372718 A1  Dec. 27, 2018

Related U.S. Application Data

(60) Provisional application No. 62/524,132, filed on Jun. 23, 2017.

(51) Int. Cl.
| | | |
|---|---|---|
| G01N 33/493 | (2006.01) | |
| G01N 33/00 | (2006.01) | |
| F21L 4/02 | (2006.01) | |
| F21V 23/04 | (2006.01) | |
| G01N 33/483 | (2006.01) | |
| F21V 33/00 | (2006.01) | |
| F21L 4/00 | (2006.01) | |

(52) U.S. Cl.
CPC ............ *G01N 33/493* (2013.01); *F21L 4/005* (2013.01); *F21L 4/022* (2013.01); *F21V 23/0414* (2013.01); *F21V 23/0442* (2013.01); *F21V 33/0068* (2013.01); *G01N 33/0047* (2013.01); *G01N 33/0054* (2013.01); *G01N 33/4833* (2013.01)

(58) Field of Classification Search
CPC ............ G01N 33/493; G01N 33/0054; G01N 33/0047; G01N 33/4833; F21L 4/005; F21L 4/022; F21V 23/0414; F21V 23/0442; F21V 33/0068
See application file for complete search history.

(56) References Cited

U.S. PATENT DOCUMENTS

| | | | |
|---|---|---|---|
| 5,709,222 A | 1/1998 | Davallou | |
| 6,638,208 B1 * | 10/2003 | Natarajan | A61F 2/0022 600/30 |
| 8,494,374 B2 | 7/2013 | Snyder | |
| 9,119,748 B2 | 9/2015 | Abraham et al. | |
| 2007/0098391 A1 | 5/2007 | Howard et al. | |
| 2009/0070046 A1 * | 3/2009 | Kenjou | G01N 33/493 702/19 |
| 2014/0323909 A1 * | 10/2014 | Kim | A61B 5/4255 600/562 |
| 2015/0212034 A1 | 7/2015 | Ansley | |
| 2015/0330958 A1 | 11/2015 | Carney et al. | |
| 2016/0008182 A1 | 1/2016 | Prokopuk et al. | |

* cited by examiner

*Primary Examiner* — Suman K Nath
(74) *Attorney, Agent, or Firm* — Luedeka Neely Group, P.C.

(57) ABSTRACT

A combination flashlight and electronic sensing device for identifying urine or feces or both and configured for facilitating stealthy detection of the same.

12 Claims, 1 Drawing Sheet

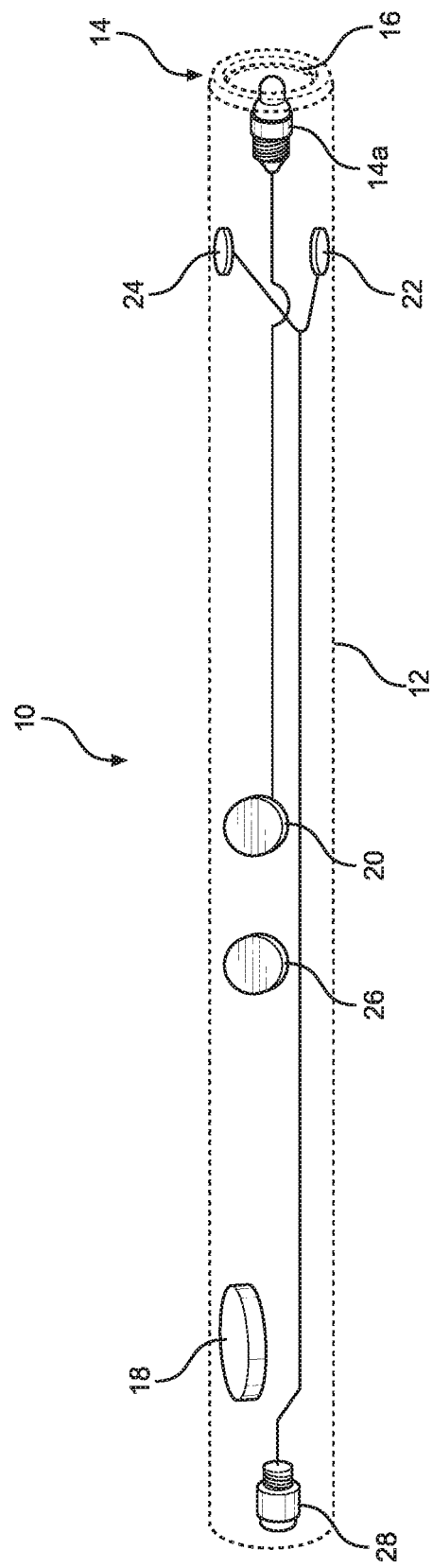

NON-CONTACT SOILAGE DETECTOR AND FLASHLIGHT

CROSS-REFERENCE TO RELATED APPLICATION

This application claims priority to U.S. Provisional Application No. 62/524,132 filed Jun. 23, 2017, entitled NON-CONTACT SOILAGE DETECTOR AND FLASHLIGHT incorporated herein by reference in its entirety.

FIELD

This disclosure relates to the field of electronic sensing devices. More particularly, this disclosure relates to a combination flashlight and electronic sensing device for identifying urine or feces or both and configured for facilitating stealthy detection of the same.

BACKGROUND

Improvement is desired in identification of soiled bedclothes, linens, diapers and the like. For example, often a mother, a nurse, or other caregiver desires to identify feces or urine soiled bedclothes, linens, diapers, or the like without physically touching or otherwise disturbing the baby, patient or others nearby.

The above and other needs are met by a combination flashlight and electronic sensing device for identifying urine or feces or both and configured for facilitating stealthy detection of the same.

SUMMARY

The present disclosure advantageously provides a device for identifying urine or feces or both.

In one aspect, the device includes a housing and an illumination source at a distal end of the housing. The illumination source is operable to provide illuminating light for visually detecting urine or feces or both.

An illumination switch is disposed on the housing and in electrical communication with the illumination source for selectively activating the illumination source. An electronic ammonia sensor is disposed on the housing proximate the distal end of the housing and operable for detecting the presence of ammonia. An electronic methane sensor is disposed on the housing proximate the distal end of the housing and operable for detecting the presence of methane.

A sensor switch is disposed on the housing and in electrical communication with the electronic ammonia sensor and the electronic methane sensor for selectively activating the electronic ammonia sensor to detect ammonia or the electronic methane sensor to detect methane or both. A sensor illumination device is in electronic communication with the electronic ammonia sensor and the electronic methane sensor, the sensor illumination device operable to illuminate in response to detection of ammonia by the electronic ammonia sensor or detection of methane by the electronic methane sensor or both.

The device of the disclosure advantageously provides a combination flashlight and electronic sensing device for identifying urine or feces or both and configured for facilitating stealthy detection of the same.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein:

FIG. 1 shows a simplified side view of a non-contact soilage detector and flashlight according to the disclosure.

DETAILED DESCRIPTION

With reference to FIG. 1, there is shown a simplified view of a combination flashlight and electronic sensing device 10 for identifying urine or feces or both and configured for facilitating stealthy detection of the same in accordance with one embodiment of the invention.

The device 10 is configured to allow mothers, nurses or other care givers to identify soiled bedclothes, diapers, linens and the like without disturbing others nearby, or disturbing infants, patients or the like.

The device 10 is configured as a small disposable flashlight or penlight with a cylindrical housing 12 having a flashlight 14 provided by an illumination source 14a (LED, incandescent or other as may be provided to provide an illuminations source) preferably behind a clear lens 16 at one end. A battery 18 is internally located within the housing 12. It will be understood that additional wiring (not shown) will be provided to enable the battery 18 to supply power to the various components. An on/off switch 20 is provided on the housing 12 and in electrical communication with the battery 18 and the illumination source 14 to enable a user to selectively turn the illumination source on or off.

The device 10 also includes a microsensor 22 configured for sensing ammonia gas at levels associated with human urine, and a microsensor 24 configured for sensing methane gas at levels associated with human feces. For example, ammonia levels of about 5 parts per million (ppm) or above, and methane levels of about 10 ppm or above.

The microsensors 22 and 24 may be disposed on the housing 12, with wiring or other electrical communication routed within the housing 12 to one or more sensor switches 26, the battery 18, and a sensor illumination device 28, such as a LED or the like. The sensor illumination device 28 is configured to illuminate when ammonia or methane is detected by the microsensors 22 and 24. Preferably, the sensor illumination device 28 is configured to illuminate in one color, such as yellow, for ammonia detection, and a different color, such as blue, for methane detection. If both methane and ammonia are detected, the sensor illumination device preferably displays a different color than the other colors, such as red.

Alternatively, separate sensor illumination devices may be provided for each of the microsensors 22 and 24, respectively. In such case, each of the separate sensor illuminations is preferably of a different coloration. In other alternate embodiments, other user notification devices could be used, such as text notifications on a display on the housing, delivery of notification to a computer via Bluetooth or wireless internet, or audible notifications provided via speakers in the housing.

The device 10 advantageously incorporates the microsensors 22 and 24 for ammonia and methane for detecting soiling by odor, together and with the flashlight 14 for detecting soiling by sight. This advantageously enables detection that urine or feces or both are present, while minimizing intrusion. The device is small and easily manipulated in the dark and in and around sites to be checked for urine and feces.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A device for identifying urine or feces or both, comprising:
    a housing;
    an illumination source at a distal end of the housing and operable to provide illuminating light for visually detecting urine or feces or both;
    an illumination switch disposed on the housing and in electrical communication with the illumination source for selectively activating the illumination source;
    an electronic ammonia sensor for detecting urine, the electronic ammonia sensor disposed on the housing proximate the distal end of the housing and operable for detecting the presence of ammonia associated with urine;
    an electronic methane sensor for detecting feces, the electronic methane sensor disposed on the housing proximate the distal end of the housing and operable for detecting the presence of methane associated with feces;
    a sensor switch disposed on the housing and in electrical communication with the electronic ammonia sensor and the electronic methane sensor for selectively activating the electronic ammonia sensor to detect ammonia or the electronic methane sensor to detect methane or both; and
    a sensor illumination device in electronic communication with the electronic ammonia sensor and the electronic methane sensor, the sensor illumination device operable to illuminate in response to detection of ammonia by the electronic ammonia sensor or detection of methane by the electronic methane sensor or both.

2. The device of claim 1, wherein the sensor illumination device illuminates in a first color when only ammonia is detected, illuminates in a second color when only methane is detected, and illuminates in a third color when both ammonia and methane are detected.

3. The device of claim 1, wherein the sensor illumination device is located adjacent a proximal end of the housing opposite the distal end.

4. The device of claim 1, wherein the sensor illumination device comprises an ammonia illumination device and a separate methane illumination device.

5. The device of claim 1, wherein the sensor switch comprises an ammonia sensor switch and a separate methane sensor switch.

6. The device of claim 1, further comprising a battery within the housing and configured to power the illumination source, the electronic ammonia sensor, the electronic methane sensor, and the sensor illumination device.

7. A device for identifying urine or feces or both, comprising:
    a housing;
    an illumination source at a distal end of the housing and operable to provide illuminating light for visually detecting urine or feces or both;
    an illumination switch disposed on the housing and in electrical communication with the illumination source for selectively activating the illumination source;
    an electronic ammonia sensor for detecting urine, the electronic ammonia sensor disposed on the housing proximate the distal end of the housing and operable for detecting the presence of ammonia associated with urine;
    an electronic methane sensor for detecting feces, the electronic methane sensor disposed on the housing proximate the distal end of the housing and operable for detecting the presence of methane associated with feces; and
    a user notification device in electronic communication with the electronic ammonia sensor and the electronic methane sensor, the user notification device operable to provide a notification to a user in response to detection of ammonia by the electronic ammonia sensor or detection of methane by the electronic methane sensor or both.

8. The device of claim 7, wherein the user notification device comprises an illumination device.

9. The device of claim 7, wherein the user notification device comprises a text display.

10. The device of claim 7, wherein the user notification device is operable to deliver notification to a computer via Bluetooth or wireless internet.

11. The device of claim 7, wherein the user notification device comprises speakers.

12. A device for identifying urine or feces or both, comprising:
    a housing;
    an illumination source at a distal end of the housing and operable to provide illuminating light for visually detecting urine or feces or both;
    an illumination switch disposed on the housing and in electrical communication with the illumination source for selectively activating the illumination source;
    a detection device comprising either a) an electronic ammonia sensor for detecting urine, the electronic ammonia sensor disposed on the housing proximate the distal end of the housing and operable for detecting the presence of ammonia associated with urine or b) an electronic methane sensor for detecting feces, the electronic methane sensor disposed on the housing proximate the distal end of the housing and operable for detecting the presence of methane associated with feces; and
    a user notification device in electronic communication with the detection device, the user notification device operable to provide a notification to a user in response to detection of ammonia by the electronic ammonia sensor or detection of methane by the electronic methane sensor.

* * * * *